(12) United States Patent
Knapp et al.

(10) Patent No.: US 11,395,653 B2
(45) Date of Patent: Jul. 26, 2022

(54) SURGICAL STAPLING DEVICE WITH IMPEDANCE SENSOR

(71) Applicant: Covidien LP, Mansfield, MA (US)

(72) Inventors: Robert Knapp, Middlebury, CT (US); Matthew Eschbach, Cheshire, CT (US); Johana Marinelli, West Hartford, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 17/076,889

(22) Filed: Oct. 22, 2020

(65) Prior Publication Data

US 2021/0153866 A1    May 27, 2021

Related U.S. Application Data

(60) Provisional application No. 62/940,337, filed on Nov. 26, 2019.

(51) Int. Cl.
*A61B 17/068*    (2006.01)
*A61B 17/072*    (2006.01)
*A61B 17/00*     (2006.01)

(52) U.S. Cl.
CPC ........ *A61B 17/0686* (2013.01); *A61B 17/072* (2013.01); *A61B 2017/00026* (2013.01); *A61B 2017/07257* (2013.01); *A61B 2017/07271* (2013.01)

(58) Field of Classification Search
CPC ...... A61B 17/068–0686; A61B 17/072; A61B 17/07207; A61B 2017/07214–07285; A61B 2017/00026; A61B 2017/07257; A61B 2017/07271

USPC .......................................................... 606/38
See application file for complete search history.

(56) References Cited

U.S. PATENT DOCUMENTS

| | | | |
|---|---|---|---|
| 5,558,671 A * | 9/1996 | Yates | A61B 17/07207 606/38 |
| 9,023,014 B2 | 5/2015 | Chowaniec et al. | |
| 9,055,943 B2 | 6/2015 | Zemlok et al. | |
| 10,052,044 B2 * | 8/2018 | Shelton, IV | A61B 5/0538 |
| 10,238,385 B2 | 3/2019 | Yates et al. | |
| 2006/0273135 A1 | 12/2006 | Beetel | |
| 2007/0175962 A1 | 8/2007 | Shelton et al. | |
| 2015/0196347 A1 * | 7/2015 | Yates | A61B 17/320016 606/48 |

FOREIGN PATENT DOCUMENTS

| | | |
|---|---|---|
| AU | 198654765 | 9/1986 |
| CA | 2773414 A1 | 11/2012 |
| CA | 2884962 A1 | 11/2015 |

(Continued)

OTHER PUBLICATIONS

European Search Report dated Mar. 30, 2021, corresponding to counterpart European Application No. 20209847.1; 8 pages.

*Primary Examiner* — Stephen F. Gerrity
*Assistant Examiner* — Linda J Hodge
(74) *Attorney, Agent, or Firm* — Carter, DeLuca & Farrell LLP

(57) ABSTRACT

A surgical stapling device includes a tool assembly including a jaw assembly and an impedance assembly. The jaw assembly includes an anvil assembly and a cartridge assembly. The tool assembly supports an impedance assembly for measuring the impedance of tissue grasped within the jaw assembly.

20 Claims, 4 Drawing Sheets

(56) References Cited

FOREIGN PATENT DOCUMENTS

| | | | |
|---|---|---|---|
| DE | 2744824 | A1 | 4/1978 |
| DE | 2903159 | A1 | 7/1980 |
| DE | 3114135 | A1 | 10/1982 |
| DE | 4213426 | A1 | 10/1992 |
| DE | 4300307 | A1 | 7/1994 |
| EP | 0041022 | A1 | 12/1981 |
| EP | 0136950 | A2 | 4/1985 |
| EP | 0140552 | A2 | 5/1985 |
| EP | 0156774 | A2 | 10/1985 |
| EP | 0213817 | A1 | 3/1987 |
| EP | 0216532 | A1 | 4/1987 |
| EP | 0220029 | A1 | 4/1987 |
| EP | 0273468 | A2 | 7/1988 |
| EP | 0324166 | A2 | 7/1989 |
| EP | 0324635 | A1 | 7/1989 |
| EP | 0324637 | A1 | 7/1989 |
| EP | 0324638 | A1 | 7/1989 |
| EP | 0365153 | A1 | 4/1990 |
| EP | 0369324 | A1 | 5/1990 |
| EP | 0373762 | A1 | 6/1990 |
| EP | 0380025 | A2 | 8/1990 |
| EP | 0399701 | A1 | 11/1990 |
| EP | 0449394 | A2 | 10/1991 |
| EP | 0484677 | A1 | 5/1992 |
| EP | 0489436 | A1 | 6/1992 |
| EP | 0503662 | A1 | 9/1992 |
| EP | 0514139 | A2 | 11/1992 |
| EP | 0536903 | A2 | 4/1993 |
| EP | 0537572 | A2 | 4/1993 |
| EP | 0539762 | A1 | 5/1993 |
| EP | 0545029 | A1 | 6/1993 |
| EP | 0552050 | A2 | 7/1993 |
| EP | 0552423 | A2 | 7/1993 |
| EP | 0579038 | A1 | 1/1994 |
| EP | 0589306 | A2 | 3/1994 |
| EP | 0591946 | A1 | 4/1994 |
| EP | 0592243 | A2 | 4/1994 |
| EP | 0593920 | A1 | 4/1994 |
| EP | 0598202 | A1 | 5/1994 |
| EP | 0598579 | A1 | 5/1994 |
| EP | 0600182 | A2 | 6/1994 |
| EP | 0621006 | A1 | 10/1994 |
| EP | 0621009 | A1 | 10/1994 |
| EP | 0656188 | A2 | 6/1995 |
| EP | 0666057 | A2 | 8/1995 |
| EP | 0705571 | A1 | 4/1996 |
| EP | 0722696 | A1 | 7/1996 |
| EP | 0737446 | A1 | 10/1996 |
| EP | 0760230 | A1 | 3/1997 |
| EP | 1952769 | A2 | 8/2008 |
| EP | 2090253 | A2 | 8/2009 |
| EP | 2090254 | A1 | 8/2009 |
| EP | 2583630 | A2 | 4/2013 |
| EP | 2586382 | A2 | 5/2013 |
| EP | 2907456 | A1 | 8/2015 |
| EP | 3231376 | A1 | 10/2017 |
| EP | 3545864 | A2 | 10/2019 |
| FR | 391239 | A | 10/1908 |
| FR | 2542188 | A1 | 9/1984 |
| FR | 2660851 | A1 | 10/1991 |
| FR | 2681775 | A1 | 4/1993 |
| GB | 1352554 | A | 5/1974 |
| GB | 1452185 | A | 10/1976 |
| GB | 1555455 | A | 11/1979 |
| GB | 2048685 | A | 12/1980 |
| GB | 2070499 | A | 9/1981 |
| GB | 2141066 | A | 12/1984 |
| GB | 2165559 | A | 4/1986 |
| JP | 51149985 | | 12/1976 |
| JP | 2001087272 | | 4/2001 |
| SU | 659146 | A1 | 4/1979 |
| SU | 728848 | A1 | 4/1980 |
| SU | 980703 | A1 | 12/1982 |
| SU | 990220 | A1 | 1/1983 |
| WO | 2008302247 | | 7/1983 |
| WO | 8910094 | A1 | 11/1989 |
| WO | 9210976 | A1 | 7/1992 |
| WO | 9308754 | A1 | 5/1993 |
| WO | 9314706 | A1 | 8/1993 |
| WO | 2004032760 | A2 | 4/2004 |
| WO | WO-2006113394 | A2 * | 10/2006 ........... A61B 5/7455 |
| WO | 2009071070 | A2 | 6/2009 |
| WO | 20150191887 | A1 | 12/2015 |
| WO | WO-2019130106 | A1 * | 7/2019 ..... A61B 17/320092 |

\* cited by examiner

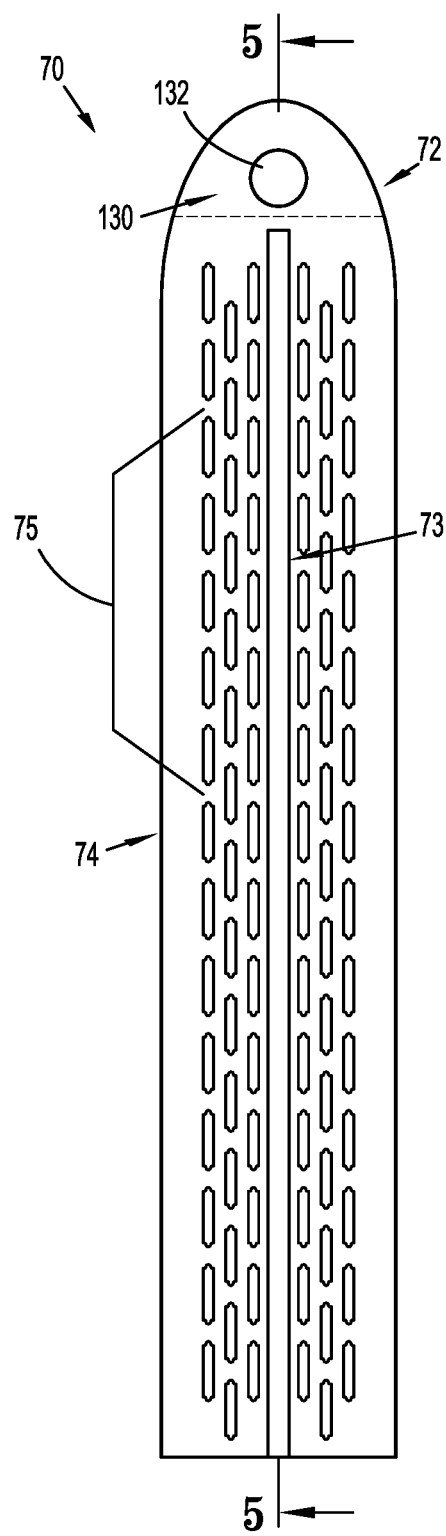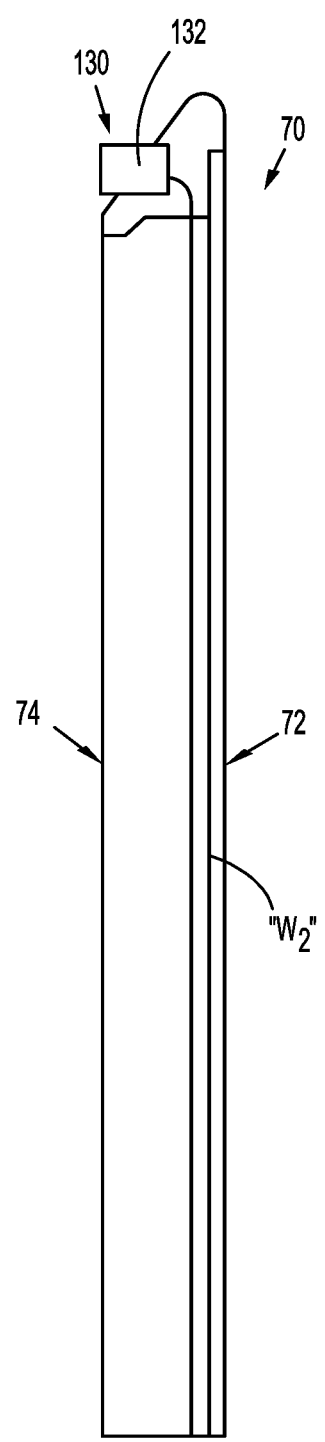
FIG. 4　　FIG. 5

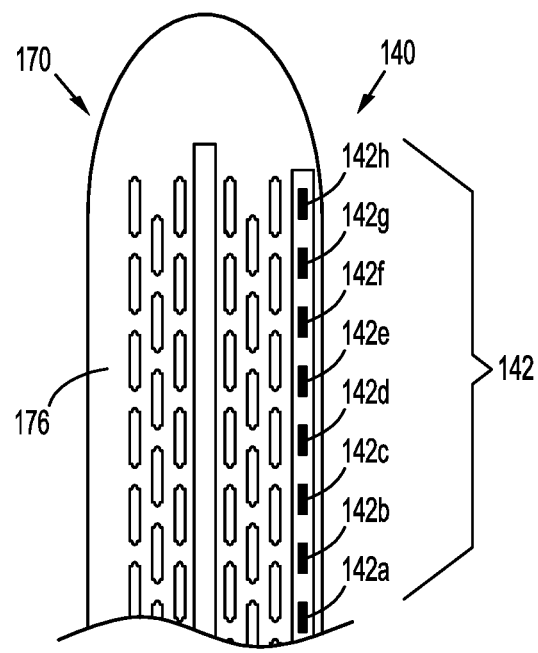
FIG. 6
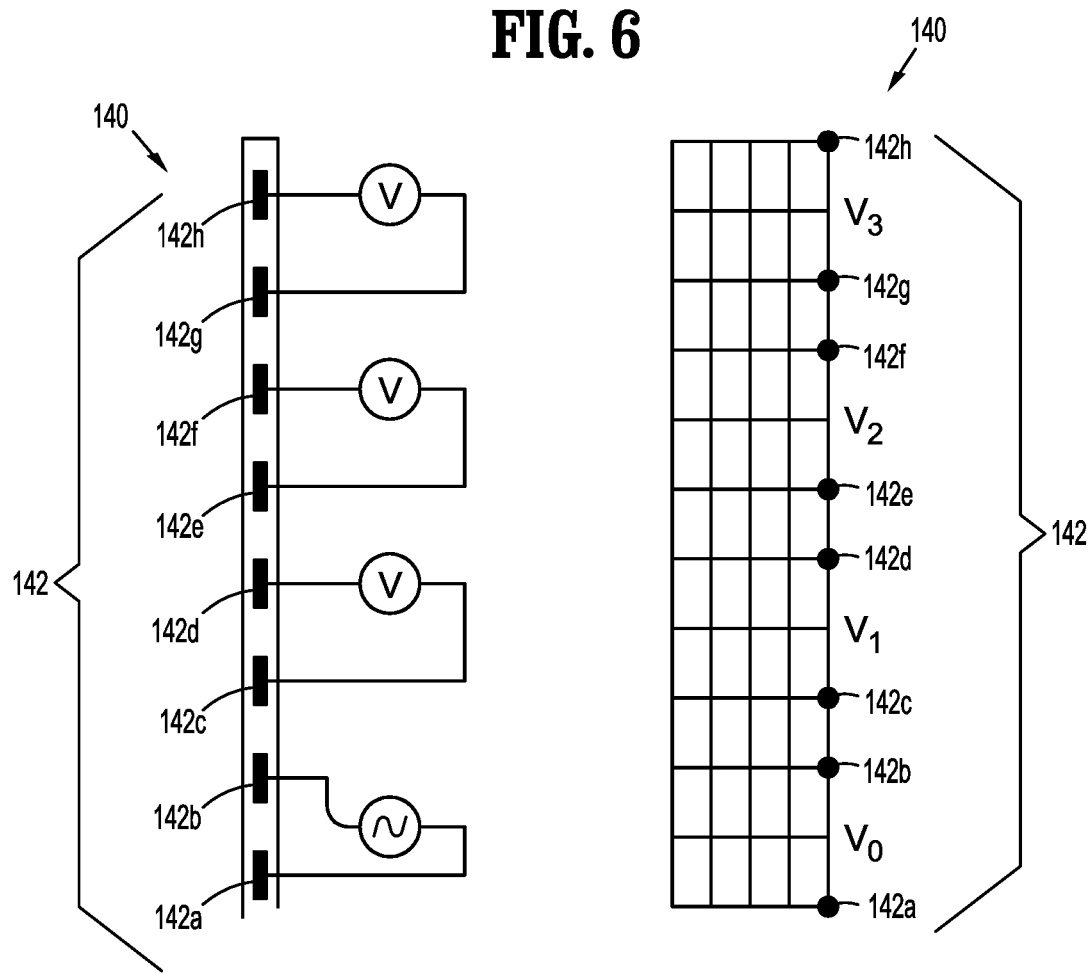
FIG. 7  FIG. 8

SURGICAL STAPLING DEVICE WITH IMPEDANCE SENSOR

CROSS-REFERENCE TO RELATED APPLICATIONS

This application claims the benefit of and priority to U.S. Provisional Patent Application Ser. No. 62/940,337 filed Nov. 26, 2019, the entire disclosure of which is incorporated by reference herein.

FIELD

The disclosure relates to surgical stapling devices. More particularly, the disclosure relates to jaw assemblies of surgical stapling devices that include impedance sensors for detecting electrical properties of tissue.

BACKGROUND

Minimally invasive surgical stapling is used in many procedures that require tissue resection, e.g., removing cancerous lung tissue or diseased bowel. Techniques for surgical stapling allow for clamping and firing of a stapler to be precisely controlled using motors and electronics. Research shows that by optimizing the time between clamping and firing, serosal tearing of the tissue may be reduced. Clinical studies show that reducing the firing speed of the stapler on thick tissue improves staple formation.

As powered stapling techniques progress, more and more is being discovered about tissue properties and their effects on surgical stapling. There are several ways to obtain tissue properties, including force measurement. However, some tissue properties cannot be obtained with a force measurement, e.g., tissue electrical properties.

Researchers have found that tissue impedance may be used to detect cancerous tissue among healthy tissue, to differentiate between tissue types, and to detect leaks, e.g., in staple lines, when used in certain circumstances. Additionally, impedance electrodes may be utilized to obtain tissue visualization (tomography). By integrating this measurement technique into surgical instruments, e.g., staplers, forceps, several important metrics may be provided to the surgeon. A surgeon may use these metrics for detecting cancer margins prior to resection to ensure complete removal of diseased tissue, for differentiating between tissue types for improving stapling firing parameters, for preventing tissue and critical organ injuries, e.g., firing across a ureter during prostate cancer surgery, and for detecting anastomotic leaks.

Therefore, it would be beneficial to have surgical stapling devices that include one or more sensors for measuring tissue impedance.

SUMMARY

A surgical stapling device including a handle assembly and a jaw assembly electrically coupled to the handle assembly is provided. The jaw assembly includes an anvil assembly, a cartridge assembly, the anvil assembly and the cartridge assembly being pivotal relative to each other between open and clamped positions, a first impedance sensor including a first electrode, the first electrode being supported by the anvil assembly, and a second impedance sensor including a second electrode. The second electrode is supported by one of the anvil assembly or the cartridge assembly. The first and second electrodes operate in combination to measure the impedance of tissue between the anvil assembly and the cartridge assembly.

In embodiments, the anvil assembly includes an anvil plate and the anvil plate defines the first electrode. The second electrode may be disposed on a distal end of the anvil assembly. The cartridge assembly may define a channel and may include a staple cartridge. The staple cartridge may be received within the channel. The second electrode may be supported on the staple cartridge. The second electrode may be supported within the channel. The staple cartridge may be removable from the channel. The second electrode assembly may further include an insulating member disposed about the second electrode.

A surgical stapling device includes a handle assembly and a jaw assembly electrically coupled to the handle assembly. The jaw assembly includes an anvil assembly and a cartridge assembly with the anvil assembly and the cartridge assembly being pivotal relative to each other. The jaw assembly further includes an impedance sensor including an array electrodes. The array of electrodes are supported by at least one of the cartridge assembly and the anvil assembly. The array electrodes includes a first set of electrodes configured to receive a current therebetween, and at least one second set of electrodes configured to measure a voltage therebetween.

In embodiments, the array of electrodes includes four sets of electrodes. The cartridge assembly may include a staple cartridge, the array of electrodes being supported on the staple cartridge.

Another surgical stapling device a handle assembly and a jaw assembly electrically coupled to the handle assembly is provided. The jaw assembly includes an anvil assembly including an anvil plate. The anvil plate forms a first electrode of a first impedance sensor. The jaw assembly further includes a cartridge assembly with the anvil assembly and the cartridge assembly being pivotal relative to each other between open and clamped positions, and a second impedance sensor including a second electrode. The second electrode is supported by the anvil assembly. The first and second electrodes operate in combination to measure the impedance of tissue between the anvil assembly and the cartridge assembly.

In embodiments, the second impedance sensor includes an insulating member. The insulating member may be disposed about the second electrode. The insulating member may be disposed between the first electrode and the second electrode. The second electrode may be supported on a distal portion of the anvil assembly.

BRIEF DESCRIPTION OF THE DRAWINGS

The accompanying drawings, which are incorporated in and constitute a part of this specification, illustrate aspects of the disclosure and, together with a general description of the disclosure given above, and the detailed description of the aspects of the disclosure given below, serve to explain the principles of the disclosure, wherein:

FIG. 4 is a schematic view of an exemplary cartridge assembly of the surgical stapling device shown in FIG. 1 according to exemplary aspects of the disclosure, including a third impedance sensor;

FIG. 5 is a schematic side view of the cartridge assembly shown in FIG. 4;

FIG. 6 is a schematic top view of a distal end of another exemplary cartridge assembly of the surgical stapling device shown in FIG. 1 according to exemplary aspects of the disclosure, including a fourth impedance sensor;

FIG. 7 is a schematic view representing the fourth impedance sensor shown in FIG. 6 during an activation of the fourth impedance sensor; and FIG. 8 is a schematic view representing measurements of the fourth impedance sensor shown in FIG. 6 during activation of the fourth impedance sensor.

DETAILED DESCRIPTION

Figure 1:
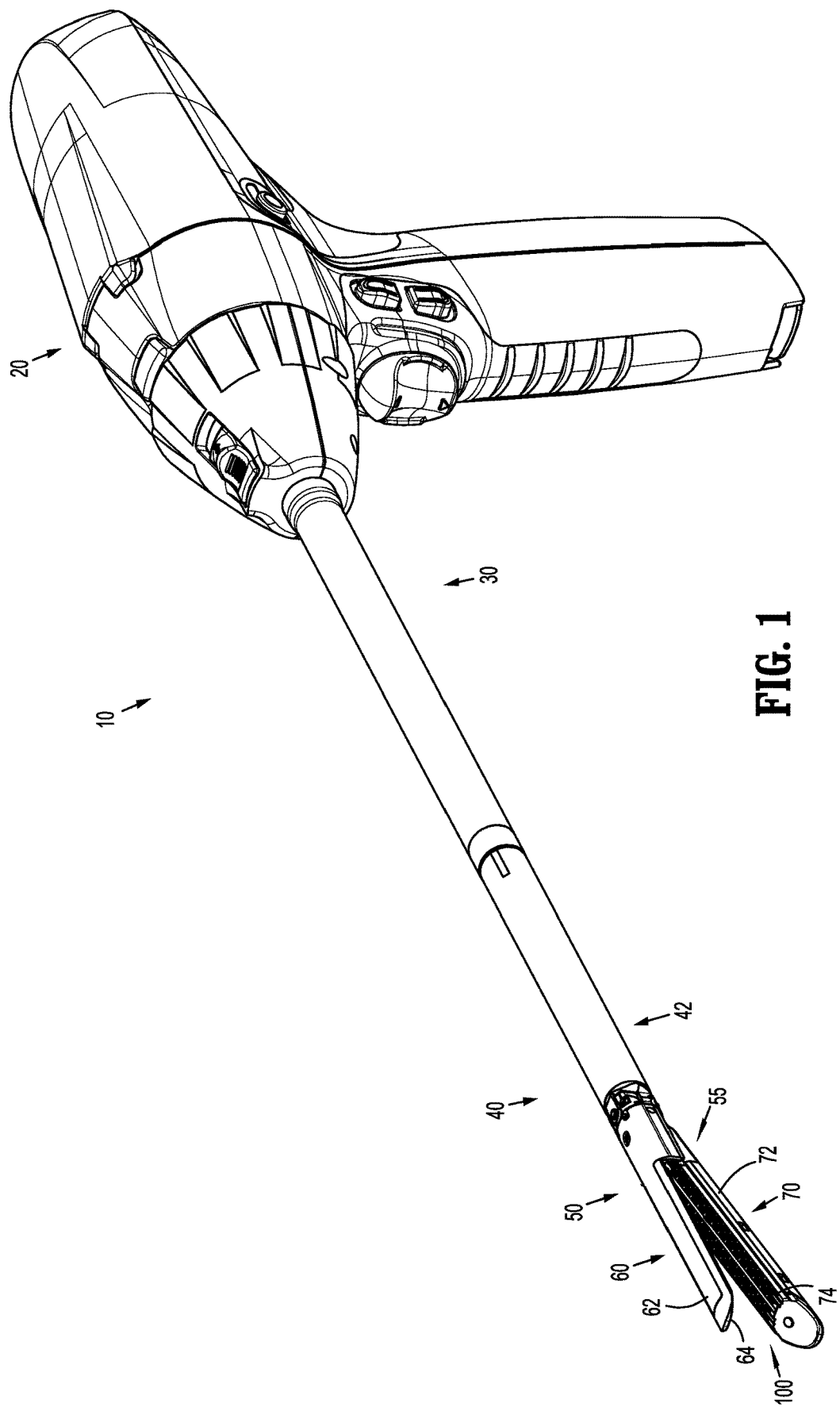
FIG. 1 is a perspective view of a surgical stapling device including a handle assembly, an adapter assembly, and a tool assembly according to exemplary aspects of the disclosure.

Aspects of the disclosed surgical stapling devices including impedance sensors will now be described in detail with reference to the drawings in which like reference numerals designate identical or corresponding elements in each of the several views. As is common in the art, the term "proximal" refers to that part or component closer to the user or operator, i.e. surgeon or clinician, while the term "distal" refers to that part or component further away from the user.

FIG. 1 illustrates a surgical stapling device according to exemplary aspects of the disclosure, shown generally as surgical stapling device 10, including a powered handle assembly 20, an adapter assembly 30 releasably secured to the powered handle assembly 20, and a loading unit 40 releasably secured to the adapter assembly 30. The loading unit 40 includes a body portion 42 and a tool assembly 50 pivotally secured to the body portion 42. The tool assembly 50 includes a jaw assembly 55 comprising an anvil assembly 60 and a cartridge assembly 70 that is pivotable relative to the anvil assembly 60.

Figure 2:
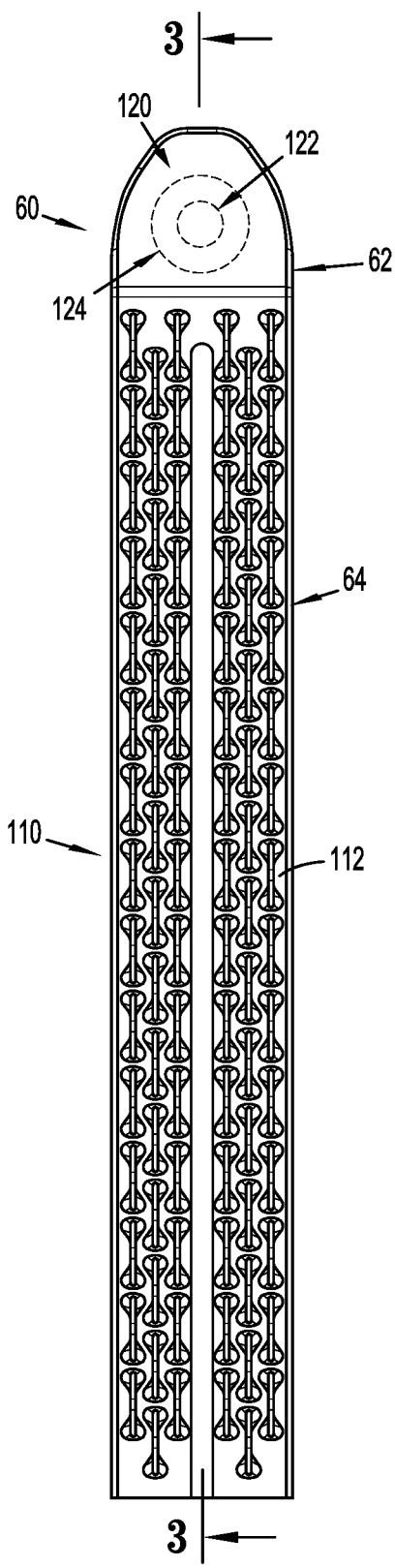
FIG. 2 is a schematic top view of an anvil assembly according to an exemplary aspects of the disclosure, including first and second impedance sensors.

The anvil assembly 60 of the tool assembly 50 of the loading unit 40 may include an anvil body 62 and an anvil plate 64 secured to the anvil body 62. The anvil plate 64 defines a plurality of staple forming pockets 63 (FIG. 2). Alternatively, the anvil body 62 and anvil plate 64, including the staple forming pockets 63, may be formed as one piece, e.g., of monolithic construction. At least the anvil plate 64 of the anvil assembly 60 is formed of a conductive metal. During a surgical procedure, the anvil plate 64 contacts tissue as tissue is grasped within the jaw assembly 55.

The cartridge assembly 70 of the tool assembly 50 of the loading unit 40 defines a channel 72 and a staple cartridge 74 is supported within the channel 72. The staple cartridge 74 defines a longitudinal slot 73 (FIG. 4) and a plurality of staple receiving pockets 75 formed on either side of the longitudinal slot 73. The loading unit 40 may be configured for a single firing, i.e., single use loading unit, or may instead be configured for multiple firings, i.e., multiple use loading unit. In a multiple use loading unit, the staple cartridge 72 is replaceable.

Although the exemplary impedance sensing assemblies will be shown and described with reference to surgical stapling device 10, and more particularly, the jaw assembly 55 of the tool assembly 50 of the surgical stapling device 10, it is envisioned that the impedance sensing assemblies may be modified for use with manually actuated surgical stapling devices having various configurations, and with powered surgical stapling devices having alternative configurations. For a detailed description of exemplary surgical stapling devices, please refer to U.S. Pat. Nos. 9,023,014 and 9,055,943. It is further envisioned that the impedance sensing assemblies may be modified for use with other surgical devices having jaw assemblies, e.g., surgical forceps, graspers, vessels sealers, etc.

Figure 3:
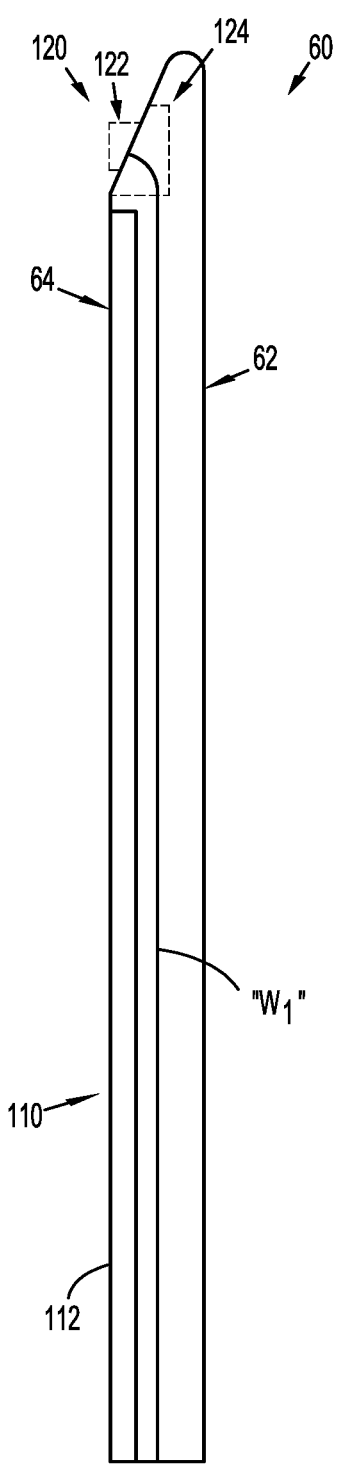
FIG. 3 is a schematic side view of the anvil assembly shown in FIG. 2.

FIGS. 2 and 3 illustrate schematic views of the anvil assembly 60. As noted above, the anvil assembly 60 includes the anvil body 62 and anvil plate 64, which may be monolithically formed. In a first embodiment, the anvil plate 64 of the anvil assembly 60 forms a first electrode 112 of a first impedance sensor 110. A second impedance sensor 120 includes a second electrode 122 and is disposed adjacent a distal end 60a of the anvil assembly 60. The second impedance sensor 120 may be received within a protective member, e.g., an insulating tube 122, to insulate the second electrode 122 of the second impedance sensor 120 from the first electrode 122 of the first impedance sensor 110. The second electrode 122 of the second impedance sensor 120 is electrically coupled to the handle assembly 20 (FIG. 1) by a wire "W1", or other electrically conductive element.

During a surgical procedure, the first impedance sensor 110 and the second impedance sensor 120 of the anvil assembly 60 operate to measure the impedance of tissue contacted by the anvil assembly 60. By including both the first and second impedance sensors 110, 120 on the anvil assembly 60, the tissue impedance may be measured while the jaw assembly 55 of the tool assembly 50 remains in an open condition (FIG. 1), i.e., without closing the jaw assembly 55.

Although the anvil assembly 60 is shown including both first and second impedance sensors 110, 120, it is envisioned that the anvil assembly 60 may include only one of the first and second impedance sensors 110, 120, and, as described in further detail below, either the first or second impedance sensor 110, 120 may operate in combination with the one or more impedance sensors of the cartridge assembly 70 to measure the impedance of the tissue grasped by the tool assembly 50.

FIGS. 5 and 6 illustrate a schematic view of the cartridge assembly 70. In certain aspects of the disclosure, a third impedance sensor 130 includes a third electrode 132 and is disposed adjacent a distal end 72 of the cartridge assembly 70. It is envisioned that the third impedance sensor 130 may be positioned anywhere along a length of the cartridge assembly 70. In some aspects of the disclosure in which the staple cartridge 74 is replaceable, the third impedance sensor 130 is secured directly within the channel 72. The third electrode 132 of the third impedance sensor 130 is electrically coupled to the handle assembly 20 by a wire "W2", or other conductive element.

The third impedance sensor 130 operates in combination with either or both of the first and second impedance sensors 110, 120 (FIG. 2) of the anvil assembly 60. More particularly, during a surgical procedure, the impedance of tissue received between the third electrode 132 of the third impedance sensor 130 of the cartridge assembly 70 and the first and/or second electrodes 112, 122 of the first and/or second impedance sensors 110, 120 of the anvil assembly 60 is measureable when the jaw assembly 55 of the tool assembly 50 is in an approximated position (not shown), i.e., closed or clamped position.

FIGS. 6-8 illustrate a schematic of a fourth impedance sensor 140 incorporated into a cartridge assembly 170. Although shown supported on one side of a staple cartridge 174 of the cartridge assembly 170, it is envisioned that the fourth impedance sensor 140 may be supported on either or both sides of the staple cartridge 174, or may additionally or instead be supported on an anvil assembly, e.g., the anvil assembly 60 (FIG. 2).

The fourth impedance sensor 140 includes an array of electrodes 142 including electrodes 142*a-h*. In some aspects of the disclosure, the fourth impedance sensor 140 includes a flex circuit. The electrodes 142*a-h* of the array of electrodes 140 are disposed along a tissue contacting surface 176 of the cartridge assembly 170.

By activating a first set of electrodes, e.g., first and second electrodes 140*a*, 140*b*, by supplying a low power AC current to the first and second electrodes 140*a*, 140*b*, voltage measurements between the remaining sets of electrodes, e.g., a voltage "V1" between the third and fourth electrodes 142*c*, 142*d*, a voltage "V2" between the fifth and sixth electrodes 142*e*, 142*f*, and a voltage "V3" between the seventh and eighth electrodes 142*g*, 142*h*, may be measured. All possible sets or a fraction of the possible sets of the electrodes 142*a-h* may be activated such that each possible set of electrodes becomes the active set. The voltage measurements measured between each of the sets of electrodes may then be combined to solve for the underlying impedance of the tissue to produce an image. The process for producing the resulting image is similar to solving a finite element analysis in mechanics. A grid may be created to solve for the current and voltage at each element, thereby producing an impedance image. The impedance image may be used to identify the type of tissue positioned within the tool assembly 50 between the anvil assembly 60 and the cartridge assembly 170. From this, a cancer margin of the tissue may be identified or detected.

It is envisioned that the disclosed impedance sensors may be used in combination with the surgical stapling device 10 (FIG. 1) or other devices having a jaw assembly to enable differentiating between tissue types for tissue specific firing algorithms. The impedance sensors may also enable detection of critical structures to prevent injuries to the structures and/or firing of the stapling device on incorrect structures, e.g., blood vessels, ureters. The impedance sensors may also facilitate detection of cancer to improve cancer margins in tissue resections, and facilitate detection of leaks as a post firing test. In addition, the impedance sensors may enable imaging tissue based on electrical properties of the tissue in a manner similar to how ultrasound is used for imaging using sound properties.

Persons skilled in the art will understand that the devices and methods specifically described herein and illustrated in the accompanying drawings are non-limiting exemplary aspects of the disclosure. It is envisioned that the elements and features illustrated or described in connection with one exemplary embodiment may be combined with the elements and features of another without departing from the scope of the disclosure. As well, one skilled in the art will appreciate further features and advantages of the disclosure based on the above-described aspects of the disclosure. Accordingly, the disclosure is not to be limited by what has been particularly shown and described.

What is claimed is:

1. A surgical stapling device comprising:
 a handle assembly; and
 a jaw assembly electrically coupled to and extending distally of the handle assembly, the jaw assembly including,
  an anvil assembly defining a plurality of staple forming pockets,
  a cartridge assembly, the anvil assembly and the cartridge assembly being pivotal relative to each other between open and clamped positions,
  a first impedance sensor including a first electrode, the first electrode being supported by the anvil assembly, and
  a second impedance sensor including a second electrode, the second electrode being supported by the anvil assembly and disposed entirely distal of the plurality of staple forming pockets, wherein the first and second electrodes operate in combination to measure the impedance of tissue in contact with the anvil assembly.

2. The surgical stapling device of claim 1, wherein the anvil assembly includes an anvil plate, the anvil plate defining the first electrode.

3. The surgical stapling device of claim 1, wherein the anvil assembly includes a distal end, the second electrode being disposed on the distal end of the anvil assembly.

4. The surgical stapling device of claim 3, wherein the second electrode further includes an insulating member disposed about the second electrode.

5. The surgical stapling device of claim 1, wherein the cartridge assembly defines a channel and includes a staple cartridge, the staple cartridge received within the channel.

6. The surgical stapling device of claim 5, wherein the staple cartridge is removable from the channel.

7. The surgical stapling device of claim 1, wherein the second impedance sensor includes an insulating member.

8. The surgical stapling device of claim 7, wherein the insulating member is disposed about the second electrode.

9. The surgical stapling device of claim 7, wherein the insulating member is disposed between the first electrode and the second electrode.

10. A surgical stapling device comprising:
 a handle assembly; and
 a jaw assembly having a proximal portion and a distal portion, the proximal portion of the jaw assembly being electrically coupled to the handle assembly, the jaw assembly including,
  an anvil assembly including an anvil plate that defines a plurality of staple forming pockets, wherein the anvil plate forms a first electrode of a first impedance sensor,
  a cartridge assembly, the anvil assembly and the cartridge assembly being pivotal relative to each other between open and clamped positions,
  a second impedance sensor including a second electrode, the second electrode being supported by the anvil assembly and spaced distal of the plurality of staple forming pockets, wherein the first and second electrodes operate in combination to measure the impedance of tissue between the anvil assembly and the cartridge assembly.

11. The surgical stapling device of claim 10, wherein the second impedance sensor includes an insulating member.

12. The surgical stapling device of claim 11, wherein the insulating member is disposed about the second electrode.

13. The surgical stapling device of claim 11, wherein the insulating member is disposed between the first electrode and the second electrode.

14. The surgical stapling device of claim 10, wherein the second electrode is supported on a distal portion of the anvil assembly.

15. The surgical stapling device of claim 10, wherein the anvil assembly includes a distal end, the second electrode being disposed on the distal end of the anvil assembly.

16. The surgical stapling device of claim 10, wherein the cartridge assembly defines a channel and a staple cartridge, the staple cartridge received within the channel.

17. The surgical stapling device of claim 16, wherein the staple cartridge is removable from the channel.

18. An end effector for a surgical stapling device, the end effector comprising:
- a proximal portion configured for electrical coupling to a handle assembly; and
- a distal portion including a jaw assembly, the jaw assembly including,
  - an anvil assembly defining a plurality of staple forming pockets,
  - a cartridge assembly, the anvil assembly and the cartridge assembly being pivotal relative to each other between open and clamped positions,
  - a first impedance sensor including a first electrode, the first electrode being supported by the anvil assembly, and
  - a second impedance sensor including a second electrode, the second electrode being supported by the anvil assembly and spaced distal of the plurality of staple forming pockets, wherein the first and second electrodes operate in combination to measure the impedance of tissue in contact with the anvil assembly.

19. The end effector of claim 18, wherein the second impedance sensor includes an insulating member.

20. The end effector of claim 19, wherein the insulating member is disposed between the first electrode and the second electrode.

* * * * *